United States Patent [19]

Charlton

[11] Patent Number: 5,300,439
[45] Date of Patent: Apr. 5, 1994

[54] METHOD, DEVICE, AND COMPOSITION FOR THE ASSAY OF IONS

[75] Inventor: Steven C. Charlton, Osceola, Ind.

[73] Assignee: Miles Inc., Elkhart, Ind.

[21] Appl. No.: 919,250

[22] Filed: Jul. 27, 1992

Related U.S. Application Data

[63] Continuation-in-part of Ser. No. 564,050, Aug. 6, 1990, abandoned.

[51] Int. Cl.$^5$ .................... G01N 21/78; G01N 33/52
[52] U.S. Cl. ....................... 436/74; 436/169; 436/79; 436/171; 436/172; 436/805; 436/810; 436/530; 436/531; 422/56; 422/57; 422/82.05; 427/2; 427/8
[58] Field of Search ................. 433/56, 57, 58, 59, 433/60, 82.05, 86; 436/8, 73, 74, 79, 166, 169, 171, 172, 805, 810; 427/2, 8; 435/530, 531

[56] References Cited

U.S. PATENT DOCUMENTS

4,645,744  2/1987  Charlton et al. .................. 436/75
4,780,411  10/1988  Piejko et al. .................... 422/56

Primary Examiner—James C. Housel
Assistant Examiner—David Redding
Attorney, Agent, or Firm—Roger N. Coe

[57] ABSTRACT

A test device and method of determining the presence or concentration of a predetermined ion, such as a cation of medical interest, like sodium, potassium, calcium, magnesium or lithium, in an aqueous test sample are disclosed. The test device includes a test pad comprising a hydrophilic indicator reagent composition capable of interacting with a predetermined ion, or electrolyte, to produce a detectable or measurable response. The hydrophilic indicator reagent composition consists essentially of a hydrophobic ion specific ionophore, a hydrophobic reporter substance, and a stabilizer polymer such as gelatin. The hydrophilic indicator reagent composition, either as a film or layer, or after incorporation into a suitable carrier matrix, provides a test pad of sufficient sensitivity to the predetermined ion to achieve an accurate and trustworthy electrolyte assay of an aqueous test sample, such as plasma or serum, by a dry phase test strip assay.

37 Claims, 1 Drawing Sheet

FIG. 1

METHOD, DEVICE, AND COMPOSITION FOR THE ASSAY OF IONS

RELATED APPLICATION

This application is a continuation-in-part application of Ser. No. 564,050, filed Aug. 6, 1990, now abandoned.

FIELD OF THE INVENTION

The present invention relates to a test device and a method of assaying an aqueous test sample for the presence or concentration of an electrolyte, or ion, especially an ion of medical interest, such as sodium, potassium, calcium, magnesium and lithium. More particularly, the present invention relates to a method and device for assaying an aqueous test sample, such as plasma or serum, for a cation by utilizing a test device having a test pad or matrix incorporated with a hydrophilic indicator reagent composition formed from a hydrophobic ionophore and a hydrophobic reporter substance. Specifically, the hydrophilic indicator reagent composition consists of a hydrophobic ion-specific ionophore, a hydrophobic reporter substance and a hydrophilic polymer compound. This hydrophilic indicator reagent composition can be incorporated into a carrier matrix, usually as a film or a layer, to provide a test pad that generates a detectable or measurable response upon contact with an aqueous cation-containing test sample. The resulting test pad provides sufficient sensitivity to a predetermined cation, or cations, to afford an accurate and trustworthy dry phase electrolyte assay of an aqueous test sample.

BACKGROUND OF THE INVENTION AND PRIOR ART

The detection or concentration measurement of an ion in an aqueous test sample has applications in numerous technologies. For example, in the field of water purification, calcium ion concentration is monitored to determine the degree of calcium saturation of an ion exchange resin deionizer. Furthermore, the measurement of sodium ion concentration and other ion concentrations in seawater is important in the preparation of drinking water aboard a ship at sea. However, among the most important ion concentration determinations are measurements related to the electrolyte levels of an individual.

For example, physicians routinely assay for the amount of potassium ion in the blood as an aid in diagnosing conditions leading to muscle irritability and excitatory changes in myocardial function and condition such as ouguria, anuria, urinary obstruction and renal failure due to shock. Since the clinical range of serum potassium is only from about 2 to about 10 millimolar (mM), with a normal range of from about 3.5 to about 5.5 mM, potassium ion measurements require particular sensitivity and precision.

Similarly, assays for sodium ion require high sensitivity and precision because the total clinical range for sodium ion is from about 120 to about 170 mM, with a normal range of from about 135 to about 155 mM. An accurate and reliable measurement of lithium levels in serum also is important because the toxic dose level of lithium ion is only slightly higher than the therapeutic level used in psychiatric treatment. Other cations, such as calcium and magnesium, are also considered medically important and must be assayed accurately in order to provide the physician with sufficient information to diagnose an abnormal condition and to institute, maintain and monitor a proper medical treatment. Although the present invention is particularly useful in the measurement of metal cations, or electrolytes, found in body fluids, other ions, especially other cations, also can be accurately and reliably detected and measured.

The measurement of potassium ion concentration in aqueous test samples, such as serum or plasma, is a widely used and important diagnostic test. A reliable and fast method of determining the concentration of a clinically important ion, like potassium ion, would advance the art of medical assays where rapid, accurate ion determinations are required. Thus, for example, if a medical laboratory technician could accurately measure the sodium, lithium, magnesium, potassium or calcium level of a whole blood sample in matter of seconds or minutes, such rapid assay results would increase laboratory efficiency and would aid the physician in diagnosis. Furthermore, an easy and accurate method of determining electrolyte concentrations in plasma or serum would allow an individual to perform testing at home in order to better maintain and monitor a physician-prescribed treatment.

Therefore, in accordance with an important feature of the present invention, the cumbersome, expensive electronic equipment that is presently used, such as ion-specific electrodes, flame photometers, atomic absorption photometers or the like, can be avoided. The present invention enables the medical practitioner, or an individual at home, simply to contact the test sample with a test device, then correlate a detectable response to the concentration of the particular ion of interest.

As stated above, the present-day methods of determining ion concentration in solution include flame photometry, atomic absorption photometry and ion-specific electrodes. However, more recently, and as will be described more fully hereinafter, dry phase test strip formats have been used to assay for ions, such as potassium. In addition, with respect to the dry phase test strips and to ion-specific electrodes, the use of certain compounds and compositions that selectively isolate a particular ion of interest from the aqueous test sample have become popular. These compounds, known as ionophores, have the capability of transporting a particular ion of interest into an electrode membrane causing a difference in potential that can be measured. The ion assay methods that utilize the selective ion/ionophore phenomenon include membrane electrodes, liquid/liquid partitioning, fluorescence and dry phase test strips.

The ion-specific electrode method of determining the ion concentration of an aqueous test sample is based on the electrical potential (EMF) generated when two solutions having different concentrations of an ion are separated by an electrically-conductive membrane. In membrane separation cells, the membrane can be a simple fretted glass barrier, allowing a small but measurable degree of ion diffusion from one solution to the other. Alternatively, a nonporous, electrically-nonconductive film, such as polyvinyl chloride, impregnated with an ionophore can be employed. In the absence of the ionophore, the nonconductive film is an insulator and no EMF can be measured. However, when blended with an ionophore, the charged ions are bound to the film and a small, measurable current can be induced to flow. Such cells are ion selective because the ionophore is selective in its affinity to a particular ion, and thus binds almost exclusively to a specific ion. Therefore, any measurable EMF is due solely to the presence of the particular ion of interest bound to the ionophore.

However, ion-specific electrodes have disadvantages. The current flowing across the membrane is sufficiently small such that the actual quantity of the ion, or its counterion, transported across the membrane is insignificant. Therefore, such small changes in ion concentration produce very small changes in EMF that require sophisticated voltmeter equipment for detection. Further, the electrical neutrality of the membrane is maintained either by a reverse flow of hydrogen ions, or by a parallel flow of hydroxyl ions. However, this flow of hydroxyl ions can reduce the specificity of the electrode towards the specific ion to be determined, and therefore is an interference that has to be minimized. In addition, a major difficulty in the use of ion-selective electrodes has been a significant reduction of assay accuracy and of speed of response over a given period of time.

Prior art disclosures of ion-specific electrodes include Simon U.S. Pat. No. 3,562,129, teaching the use of porous membranes, like glass frits, impregnated with macrocyclic derivatives of amino and oxy-acids, in ion-specific electrodes. These electrodes are said to be effective in measuring ion activities. U.S. Pat. No. 4,053,381, issued to Hemblen et al., discloses a similar technology, and utilizes an ion-specific membrane with ion mobility. Similarly, Simon et al., in U.S. Pat. No. 3,957,607, discloses a process for the electrochemical determination of cations by utilizing an electrode having a membrane containing neutral ionophores capable of forming lipid soluble complexes with cations.

Another method of using ionophores in ion determination is liquid/liquid partitioning. Eisenman et al., *Membrane Biol.*, 1:294–345 (1969) teaches the selective extraction of cations from aqueous solutions into organic solvents by macrotetralide actin antibiotics. In the Eisenman et al. procedure, a hydrophobic ionophore is dissolved in a water-immiscible organic solvent. Then, the organic solvent phase containing the antibiotics is shaken with an aqueous solution containing cationic salts of lipid soluble, colored anions, such as picrates and dinitrophenolates. The intensity of color developed in the organic phase is measured spectrophotometrically to indicate the amount of extracted salt. Phase transfer has also been studied by Dix et al., *Angew. Chem. Int. Ed. Engl.*, 17S:857 (1978) and discussed in reviews including Burgermeister et al., *Top Curr. Chem.*, 69:91 (1977); Yu et al., "Membrane Active Complexones", Elsevier, Amsterdam (1974); and Duncan, "Calcium in Biological Systems", Cambridge University Press (1976).

The partitioning of a compound between liquids is rapid and effective because the mobility of the ionophore carrier and ions allows the transported species to diffuse rapidly away from the interface. Such a mechanism is normally impossible in the solid phase because of the rigidity, immobility and essentially zero diffusion of ions in a solid phase.

Another method used to detect and measure ion concentrations with an ionophore is disclosed in U.S. Pat. No. 4,367,072. The method disclosed the use of a chromogenic ionophore, i.e., an ionophore covalently linked to a chromogen. A charged chromogen-ionophore complex having the same charge as the ion to be determined is also taught. In use, a chromogenic ionophore, or a charged chromogen-ionophore complex, is added to a liquid sample and the color of the solution is monitored spectrophotometrically. It is disclosed that the ionophore can be incorporated into a carrier such as paper, synthetic resin, film, and the like.

As illustrated by the above-cited prior art, at present, diagnostic assays for the determination of electrolytes, such as sodium, potassium and lithium, routinely are measured by ion selective electrodes or by flame photometry. However, more convenient assay methods for electrolytes have become available. Dry phase reagent strips are available for the colorimetric determination of potassium ion in serum or plasma, but not whole blood, on a SERALYZER ® reflectance photometer, with both the reagent strips and the instrument marketed by Miles Inc., Elkhart, Ind. In this commercial procedure, it is necessary to separate the serum or plasma from the coagulated or packed cells of the whole blood sample. The dry phase reagent strip technology is disclosed in U.S. Pat. Nos. 4,540,520; 4,552,697; 4,649,123; 4,645,744; and 4,670,218.

Therefore, typically methods of measuring cation concentration with ionophores have required the transport of the ion by the ionophore either into a liquid organic phase (phase transfer measurements), or through an ion selective membrane containing an ionophore (electrodes or optodes). In the dry reagent strip method, the ionophore and an indicator compound are isolated within a matrix and the transport of the ion of interest into the matrix produces a detectable colorimetric response.

For example, Charlton et al. in U.S. Pat. No. 4,649,123 teaches incorporating finely divided globules of a hydrophobic mixture including a hydrophobic vehicle, like polyvinyl chloride, or a water-insoluble liquid, like dioctylphosphate or a nitrophenyl ether, into a hydrophilic carrier matrix. The globules contain an ionophore and an indicator compound, i.e., a reporter substance, and are formed by preparing an emulsion between the hydrophobic mixture and water. The emulsion then is coated onto a support member and the water evaporated leaving the the finely divided hydrophobic globules. Alternatively, the emulsion can be coated onto filter paper, then the water is evaporated and the coated filter paper is affixed to a support. In either case, the test pad of the test device comprises finely-divided globules of a hydrophobic mixture, containing an ionophore and a reporter substance in a hydrophobic vehicle, applied to or incorporated in the matrix. Similarly, Gantzer et al. in U.S. Pat. No. 4,670,218 disclose incorporating the ionophore and the reporter substance directly into a porous carrier matrix from a homogeneous, nonaqueous, hydrophobic composition, as opposed to an emulsion. The method of Gantzer then requires a second manipulative step in order to incorporate a water-soluble buffer compound into the carrier matrix.

The exception to the requirement of isolating the ionophore in a hydrophobic, or organic, phase is described by Feinstein et al., in *Proc. Nat. Acad. Sci. USA*, 68(9):2037-2041 (Sept. 1971). Feinstein et al. disclose the formation of a cation-ionophore complex in water in the presence of the anionic form of two fluorescent dyes, 1-anilino-8-naphthalene sulfonate (ANS) and 2-p-toluidinyl-6-naphthalene sulfonate (TNS). The method of Feinstein includes antibiotics, such as valinomycin and the macrotetralide actins, as the ionophores. However, the method used by the authors to produce the aqueous solutions is not clearly described. In general, the authors theorize that the observed increase in fluorescence depolarization is due to the binding sites of the cation-ionophore complex becoming saturated, but also theorize that the depolarization is caused by energy transfer between fluorophore molecules within a micelle or caused by dye interaction with aggregates of cation-ionophore complexes. Feinstein therefore proposes that a cation ionophore complex can be detected in an aqueous environment. This proposal is contrary to the prevailing theory that the stability of such cation-/ionophore complexes are drastically reduced by the addition of water to an organic solution containing the complexes.

Another exception to the requirement of isolating an ionophore in a hydrophobic, or organic, phase is disclosed Gibbons U.S. Pat. No. 4,820,647. Gibbons disclosed the wet phase diagnostic detection of metal ions with an aqueous solution including an ionophore, a reporter substance and a micelle-forming material. The micelle-forming material acts to solubiuze the hydrophobic ionophore and reporter substance.

Other prior art includes Vogtle et al., U.S. Pat. No. 4,367,072, disclosing a color change upon the addition of an ion-containing test sample to a solution of hydrazinium hydrochloride dissolved in methanol/water and mixed with molar amounts of a crown ether. A change of the absorption (brightening) is observed because the dye is displaced from its inclusion complex by a cation, such as potassium or sodium.

Therefore, in summary many methods are known for assaying ions in solution. Instrumental methods include such sophisticated techniques as ion-specific potentiometry, flame photometry and atomic absorption photometry. In addition, the use of ionophores that selectively complex with a specific ion has led to five additional approaches: ion selective electrodes, liquid/liquid partitioning, fluorescence enhancement, chromophore labeled ionophores and test strips. However, prior to the present invention, very few of the assay methods provide the user with rapid and accurate assay results by simply contacting a test sample with a test device. The present invention permits the assayer simply to contact an aqueous test sample with a test device and to observe a detectable or measurable change in color or other detectable response.

As will be described more fully hereinafter, the method of the present invention allows the fast, accurate and trustworthy ion, or electrolyte, assay of aqueous test samples by utilizing a test strip that includes a test pad comprising a new hydrophilic indicator reagent composition. The hydrophilic indicator reagent composition consists essentially of a hydrophobic ionophore, a hydrophobic reporter substance and a hydrophilic polymer compound, such as gelatin. Surprisingly and unexpectedly, and in contrast to the prior art, it is not necessary to include the ionophore and the reporter substance in a hydrophobic phase or vehicle in order to mediate the color transition or other detectable change that occurs in response to the ionophore complexing with the electrolyte. The hydrophilic indicator reagent composition of the present invention, either as a layer or film, or after incorporation into a hydrophilic carrier matrix, provides a test pad of sufficient stability and of sufficient sensitivity to a predetermined electrolyte to afford an accurate and trustworthy electrolyte assay of aqueous test samples, such as plasma or serum, by a dry phase test strip. Surprisingly and unexpectedly, the method and device of the present invention provide an accurate ion assay without isolating the ionophore in a hydrophobic organic phase.

SUMMARY OF THE INVENTION

In brief, the present invention is directed to a new and improved test device, a method manufacturing the test device, and a method of determining the presence or concentration of a predetermined component in a test sample. The device includes a test pad comprising a hydrophilic indicator reagent composition that interacts with a predetermined test sample component, like an electrolyte, to produce a detectable response. For laboratory and home use, the hydrophilic indicator reagent composition produces a response that is detectable visually or by instrument. The new and improved test device of the present invention consists of a hydrophilic indicator reagent composition either as a film or a layer, or incorporated a suitable hydrophilic carrier matrix, such as filter paper. The carrier matrix contains hydrophilic indicator reagent composition distributed homogeneously throughout and maintains carrier matrix penetrability by the test sample to be assayed. The hydrophilic indicator reagent composition consists of a hydrophobic ionophore, a hydrophobic reporter substance and a hydrophilic polymer compound, such as gelatin.

Surprisingly and unexpectedly, it has been demonstrated that the hydrophilic indicator reagent composition, either as a film or layer, or after incorporation into a suitable carrier matrix, provides a sufficiently stable dry phase test strip and provides a sufficiently differentiable and resolvable color transition, to permit the sensitive detection of a low electrolyte concentration, like a potassium ion concentration of from 0 to about 10 mMol/L (millimoles per liter). Therefore, and in accordance with an important feature of the present invention, the qualitative or quantitative determination of an electrolyte concentration between 0 mMol/L and about 200 mMol/L in plasma or serum or in other aqueous test samples is accomplished. By utilizing the test device of the present invention in clinical test methods, the qualitative or quantitative concentration of an ion, such as sodium, calcium, lithium, magnesium or potassium, can be deterudned accurately because the color resolution and differentiation exhibited by a test pad comprising the hydrophilic indicator reagent composition demonstrates sufficient sensitivity for the low concentration determination of ions. Furthermore, surprisingly and unexpectedly, the new and improved test device allows the detection and measurement of a predetermined ion, such as potassium, sodium, calcium, magnesium or lithium, in nonbiological aqueous test samples.

Therefore, it is an object of the present invention to provide a new and improved solid state test device and method of determining the relative concentration of a predetermined chemical compound in a liquid.

Another object of the present invention is to provide a simple, trustworthy, accurate and reproducible method of assaying plasma, serum or other aqueous test samples for a predetermined ion, or electrolyte.

Another object of the present invention is to provide a new and improved electrolyte interactive test device for interaction with a predetermined electrolyte in a test fluid to produce a visible response, such as a change in color, indicative of the electrolyte concentration in the test fluid.

Another object of the present invention to provide a method of assaying plasma or serum of a whole blood sample, or other aqueous test samples, for a predetermined ion, or electrolyte, such as sodium or potassium.

Another object of the present invention is to provide a method of assaying plasma, serum or other aqueous test samples that provides sufficient visual color differentiation and resolution, and therefore sufficient sensitivity, to low electrolyte concentrations.

Yet another object of the present invention is to provide a method of assaying plasma, serum or other aqueous test samples that is sensitive to, and that quantitatively discriminates between, an electrolyte level of from 0 mMol/L to about 200 mMol/L.

Another object of the present invention is to provide a method of assaying serum or plasma or other aqueous test samples, that utilizes a test device including a test pad containing a hydrophilic indicator reagent composition.

Another object of the present invention is to provide a method of assaying plasma, serum or other aqueous test samples by utilizing a hydrophilic indicator reagent composition that, when used as a film or a layer, or after incorporation into a suitable hydrophilic carrier matrix, can interact with a predetermined electrolyte and undergo a detectable or measurable color transition to establish the presence of or measure the concentration of the electrolyte in a test sample.

Another object of the present invention is to provide a test device including a test pad, comprising a hydrophilic indicator reagent composition, either as a film or a layer, or incorporated into a carrier matrix, that can interact with a predetermined electrolyte and undergo a visually or instrumentally differentiable and resolvable color transition to allow the quantitative determination of the predetermined electrolyte concentration in serum, plasma or other aqueous sample at levels between 0 mMol/L and about 200 mmol/L.

Another object of the present invention is to provide a test device including a test pad, comprising a hydrophilic indicator reagent composition consisting of a hydrophobic ionophore capable of forming a complex with the predetermined electrolyte of interest, a hydrophobic reporter substance capable of interacting with the ionophore/electrolyte complex to produce a detectable or measurable response, and a hydrophilic polymer compound, such as gelatin.

Another object of the present invention is to provide a new and improved test device, and a method of manufacturing the test device, including a test pad comprising a hydrophilic indicator reagent composition capable of interacting with a predetermined chemical compound in an aqueous test sample.

Another object of the present invention is to provide a method of assaying for a predetermined electrolyte by incorporating a hydrophilic indicator reagent composition into a hydrophilic carrier matrix to provide a dry phase detection device of sufficient sensitivity to allow the detection and measurement of a low concentration of the electrolyte.

Another object of the present invention is to provide a new and improved test device and method of manufacturing the test device for sensing the presence of a predetermined electrolyte in an aqueous sample, wherein the electrolyte is capable of interacting with a test pad comprising a film or layer of a hydrophilic indicator reagent composition, said hydrophildc indicator reagent composition consisting of a hydrophobic ionophore capable of forming a complex with the predetermined electrolyte, a hydrophobic reporter substance capable of interacting with the ionophore-electrolyte complex to produce a detectable or measurable response, and a hydrophilic polymer compound, such as gelatin.

Another object of the present invention is to provide a new and improved test device for the accurate quantitative analysis of an electrolyte, like sodium, lithium, potassium, calcium or magnesium, in a test sample within about six minutes.

BRIEF DESCRIPTION OF THE DRAWINGS

The above and other objects and advantages and novel features of the present invention will become apparent from the following detailed description of the invention illustrated in the accompanying FIGURE demonstrating the accurate and sensitive quantitative electrolyte assays achieved by the device and method of the present invention wherein.

DETAILED DESCRIPTION OF THE INVENTION

In accordance with the method of the present invention, the qualitative or quantitative assay for a predetermined electrolyte, including sodium, potassium, lithium, magnesium or calcium, in serum, plasma and other aqueous test samples is accomplished by utilizing a test device including a test pad comprising a hydrophilic indicator reagent composition. By employing the test device of the present invention the color differentiation and color resolution of the color transitions provided by different concentrations of the electrolyte are sufficient to provide a sensitive and accurate assay for the electrolyte concentration in a test sample. In addition, the sensitivity of the assay is sufficient to allow the accurate determination of a low concentration of electrolyte. The sensitivity to low electrolyte levels afforded by the method of the present invention is especially useful in plasma and serum assays.

Prior to the present invention most investigators utilized the ability of an ionophore to transport a specific ion either into an organic liquid phase, or through an ion selective membrane, or into a solid hydrophobic environment. Researchers conducting investigations into the solid phase ion test strips also attempted, relatively unsuccessfully, to increase the reactivity of nonporous film formats.

Therefore, present day commercial assays for a predetermined electrolyte, such as potassium ion, are based on a colorimetric, ionophore-mediated, cation/proton exchange reaction between an aqueous phase and an organic phase. Such assays result in the quantitative measurement of the color transition produced when potassium ions in a diluted aqueous test sample are exchanged simultaneously for hydrogen ions from a reporter substance. The test pad of the present day electrolyte test device includes a carrier matrix containing a hydrophobic organic phase and the components of an aqueous phase, like a buffer. When an aqueous test sample is applied to the test pad, the components of the aqueous phase are solubilized and the aqueous phase is reconstituted. An ionophore selective for potassium ions, 2,3-(naphtho)-15-crown-5, present in the organic phase, mediates a transfer of potassium ions from the aqueous phase to the organic phase. Charge neutrality in the hydrophobic organic phase is maintained by the simultaneous loss of a proton from a reporter substance, the indicator dye, e.g., 7-decyl- MEDPIN, in the organic phase. Deprotonation of the dye results in the appearance of an absorption peak at 640nm. The overall reaction scheme is shown below:

The degree and intensity of the color transition due to the above reaction is proportional to the amount of potassium ion in the test sample and is monitored by reflectance spectroscopy at 640 nm with reflectance measurements taken at five second intervals. Results can be displayed digitally by an instrument in units of mMol/L.

The present-day potassium ion test strip assay thus combines the convenience of dry phase chemistry with a simple, quick and highly-selective method of quantitatively determining the concentration of potassium. However, in accordance with the present invention, it has been found that conventional teachings concerning the requirement of an organic, or hydrophobic, phase or vehicle in the test device for a successful ion/ionophore-based assay were erroneous. The present test device and method utilize a hydrophilic indicator reagent composition, used either as a film or a layer, or incorporated into a suitable hydrophilic carrier matrix, as the test pad of the test device. In addition, the dry phase test strips of the present invention are compatible with conventional analyzers, including diagnostic analyzers based on absorbance measurements of a dry phase test strip that contacts a body fluid sample.

It should be noted that the term "hydrophilic" is defined as that physical property of a substance to have a strong or pronounced tendency to bind or absorb water. Therefore, the term hydrophilic includes those materials that swell or form reversible gels upon contact with water; that are wettable or permeable by water; or that form aqueous solutions. In contrast, the term "hydrophobic" describes the physical property of a substrate not to adsorb or absorb water.

The hydrophilic indicator reagent composition of the present invention includes a hydrophobic ionophore. Ionophores are well known in the art, and, as organic molecules, generally exhibit minimal water solubility. The term "ionophore" includes organic molecules capable of selectively forming a complex with a particular ion to the substantial exclusion of forming complexes with other ions. For example the cyclic polyether 2,3-naphtho-1,4,7,10,13-pentaoxacyclopentadeca-2-ene, also known as 2,3-naphtho-15-crown-5, selectively interacts with potassium ions to form a cationic complex. Therefore, the term "ionophore" includes neutral, electron-rich compounds that are capable of complexing with cations. Accordingly, the term includes multidentate cyclic compounds that contain electron-rich donor atoms, like oxygen or nitrogen, in their cyclic chains. Such multidentate cyclic compounds can be monocyclic or polycyclic. Alternatively, the ionophore can be an open chain compound containing donor atoms. Thus, included in the term ionophore are monocyclic ion-specific compounds known as coronands; open chain ion-specific compounds known as podands; and antibiotic type ionophores such as valinomycin and macrotetralide actins. The coronand class, referred to as crown ethers, are particularly useful ionophores.

All members of the class of compounds generally known as ionophores can be used in the method and device of the present invention. Numerous examples of ionophore/ion pairs can be found in the literature. For example, U.S. Pat. Nos. 4,649,123 and 4,670,218, herein incorporated by reference, include a full discussion and several nonlimiting examples of the various types of ionophores that are also useful in the present invention. In general, ionophores are capable of complexing with ions, usually a specific ion, and of transporting the ion through lipid membranes or into an organic phase as an ionophore/ion complex. This property, i.e., the ability to transport an ion into a hydrophobic phase, is used to distinguish ionophores as a class from the broader class of compounds known as "chelates." Chelates, while technically a broader classification, are commonly considered as charged, water-soluble molecules capable of complexing ions and solubilizing the ions in aqueous media.

Examples of ionophores found especially useful in the present invention are listed in TABLE I. It should be understood that TABLE I is merely illustrative of nonlimiting examples of ionophores that are useful in the present invention, and that several other, unlisted ionophores known to workers skilled in the art also can be included in the hydrophilic indicator reagent composition. TABLE I also lists the cation most selectively complexed by each ionophore. It should be noted that an individual ionophore, although considered to specifically complex with a particular cation, may also complex with other cations to varying degrees. Structural formulas for some of the ionophores listed in TABLE I can be found in U.S. Pat. No. 4,639,123.

TABLE I

| Ionophores | |
|---|---|
| Ionophore | Specific Cation |
| 1,1,1-tris[1'-(2'-oxa-4'-oxo-5' aza-5'-methyl)dodecanyl]propane | Na+ (sodium) |
| N,N'-dibenzyl-N,N'-diphenyl-1,2-phenylenedioxydiacetamide | Na+ |
| 6,7,9,10,18,19-hexahydro-17-n-butyl dibenzol[b,k][1,4,7,10,13]pentaoxa-cyclohexadecane-18-yl-oxyacetic acid | Na+ |
| 2,3-naphtho-1,4,7,10,13-pentaoxa-cyclopentadeca-2-ene | K+ (potassium) |
| N,N'-diheptyl-N,N',5,5-tetramethyl-3,7-dioxanonane diamide | Li+ (lithium) |
| N,N'-diheptyl-5,5-dimethyl-N,N'-di(3-oxapentyl)-3,7-dioxanane diamide | Li+ |
| cis-N,N,N',N'-tetraisobutyl-1,2-cyclohexane dicarboxamide | Li+ |
| diethyl-N,N'-[(4R,5R)-4,5-dimethyl-1-8-dioxo-3,6-dioxaoctamethylene]-bis(12-methylaminododecanoate) | Ca++ (calcium) |
| 15-crown-5 | Na+, K+ |
| Valinomycin | K+ |
| 4,7,13,16,21,24-hexaoxa-1,10-diaza-bicyclo[8,8,8]hexacosane (KRYPTOFIX ® 222) | K+ |
| 4,7,13,16,21-pentaoxa-1,10-diaza-bicyclo[8,8,5]tricosane (KRYPTOFIX ® 221) | Na+ |
| 18-crown-6 | K+ |
| dibenzo-18-crown-6 | K+ |
| dicyclohexano-18-crown-6 | K+ |

TABLE I-continued

| Ionophores | |
|---|---|
| Ionophore | Specific Cation |
| 4,7,13,18-tetraoxa-1,10-diaza-bicyclo[8,5,5,]eicosane (KRYPTOFIX ® 211) | $Li^+$ |
| 12-crown-4 | $Li^+$ |
| N,N'-diheptyl-N,N'-dimethyl-1,4-butanediamide | $Mg^{++}$ (magnesium) |
| bis[12-crown-4-methyl] methyldodecylmalonate | $Na^+$ |
| Monesin | $Na^+$ |

(KRYPTOFIX ® is a trademark of E. Merck, Darmstadt, West Germany.)

Although these specific ionophores can be used advantageously in the test device of the present invention, they are presented only as examples and other ionophores, or mixtures thereof, also can be used as long as the ionophore has sufficient electrolyte specificity for the particular ion of interest.

The hydrophilic indicator reagent composition of the present invention also includes a hydrophobic reporter substance. The reporter substance provides a detectable response upon formation of the ionophore/ion complex. A reporter substance usually is capable of interacting with an ionophore/ion complex to produce a color transition or other detectable response in the test device. In general, "interacting" means any mutual action between a reporter substance and an ionophore/ion complex that leads to a detectable response. For example, the interaction between an ionophore/ion complex and a reporter substance having a dissociable proton causes the reporter substance to lose a proton thus producing a detectable response.

The expression "detectable response" is defined as a change in a test device that is capable of being perceived, either visually or instrumentally, and that can be correlated to the concentration of a specific ion in an aqueous test sample. Therefore, detectable responses include, but are not limited to, a change in color, fluorescence, reflectance, pH, chemiluminescence or infrared spectra. A colorimetric response is preferred, although a fluorometric response is useful with suitable measuring equipment. An example of a reporter substance interacting with an ionophore/ion complex and generating a detectable response is the change of p-nitrophenol from a colorless to a colored form by the ion/ionophore complex.

The reporter substance can be a single compound that ionizes in response to the formation of the ionophore/ion complex, or the reporter substance can be a mixture of compounds that produce a detectable product when a reaction chain is triggered by the presence of the ion/ionophore complex. Thus, if the electrolyte of interest is not present in the test sample, no ionophore/ion complex results and the reporter substance remains unchanged. Hence, no detectable response is observed. Alternatively, when the particular ion of interest is present, the resulting ionophore/ion complex interacts with the reporter substance and the reporter substance undergoes a detectable change.

To achieve the full advantage of the present invention, the reporter substance is a neutral compound having a dissociable proton. Furthermore, the reporter substance is capable of dissociating upon interaction with the ionophore/ion complex to produce a detectable response. The preferred reporter substances can be referred to as having an acidic proton. Therefore, under suitable pH conditions, the proton of the reporter substance dissociates upon formation of the ionophore/ion complex to produce the detectable response.

With the loss of the dissociable proton, the reporter substance has a negative electrical charge, thereby causing a change in the electron distribution in the reporter substance that produces the detectable response. The expression "reporter substance" includes both organic compounds having a dissociable proton, for example, phenolic compounds, like p-nitrophenol, that are relatively colorless in the nonionized state, but are colored upon loss of the dissociable proton; and organic fluorescent compounds that produce either more or less fluorescence upon a change in electron distribution. The reporter substance also can be a compound that can trigger a detectable response when combined with other compounds. For example, the change in electron distribution in the reporter substance, caused by interaction with the ionophore/ion complex, can in turn facilitate the interaction of the reporter substance with another component that would then produce a detectable response.

It has been found that reporter substances that contain an aromatic hydroxyl moiety, i.e., a phenolic-type compound having a proton that can dissociate from the molecular to produce a detectable response, are preferred in the method of the present invention. Two classes of indophenol reporter substances of this type have been described in U.S. Pat. Nos. 4,540,520 and 4,552,697, and are hereby expressly incorporated by reference. A more comprehensive discussion of suitable reporter substances which can be used in the method of the present invention can be found in U.S. Pat. Nos. 4,649,123 and 4,670,218. However, other classes of reporter substances also are suitable for use in the present invention, including triphenylmethanes, such as tetrabromophenolphthalein decyl ester (TBDE), and the fluoresceins, such as methyl eosin, fluorescein esters, 5 7-hydroxy coumarins, resorufins, pyren-3-ols, and flavones. Other suitable dyes include phenolphthalein, bromocresol purple, cresophthalein, chlorophenol red, tetrabromophenol blue, thymophthalein and eosin-5-maleamic acid.

In general, reporter substances that have a dissociable proton are preferred for the detection or measurement of the presence or concentration of a cation in a test sample. Particularly preferred is the indophenol, 7-(n-decyl)-2,-methyl-4-(3',5'-dichlorophen-4'-one)indophenol, referred to herein as 7-decyl MEDPIN. Other suitable reporter substances include 2-methyl-4-(3',5'-dichlorophen-4'-one)indonaphth-1-ol (MEDPIN), tetrabromophenolphthalein decyl ester (TBDE), and methyl(tetrabromo fluorescein) (methyl eosin).

It should be noted that although these specific reporter substances have been used advantageously in the test device and method of the present invention, other reporter substances, or mixtures thereof, also can be used as long as the reporter substance changes color, or undergoes some other detectable change, in response to an interaction between the ion/ionophore complex and the reporter substance.

In contrast to the mixture of Charlton et al. in U.S. Pat. No. 4,649,123, which does not contain any stabilizer, the hydrophilic indicator reagent composition of the present invention must include a hydrophilic polymer compound, such as gelatin, in an amount of from about 2% to about 20% by weight of the composition.

It is theorized that the hydrophilic polymer compound either helps maintain the homogeneous dispersion of the hydrophobic reporter substance and the hydrophobic ionophore in an aqueous solution or helps solubilize these components in water.

As indicated previously, a hydrophobic organic phase was necessary in the prior art dry phase test strips to isolate the ionophore and the reporter substance from the aqueous phase produced by contact of the test strip with the test sample. The primary function of the hydrophobic organic phase or vehicle was to increase the detectable response of the test device. It has been speculated that the hydrophobic phase interacts with the ionophore/ion complex to overcome the strong attraction of ions into the aqueous phase, and therefore to stabilize the ionophore/ion complex when the complex is formed in the hydrophobic phase. Surprisingly and unexpectedly, the hydrophilic polymer compound of the present invention may perform a function similar to the hydrophobic organic phase of the prior art test strips because the test strip of the present invention demonstrates a sufficiently detectable or measurable response to the predetermined ion of interest to allow the accurate and reliable assay of low concentrations of clinically significant ions.

In selecting a hydrophilic polymer compound it is important that the substance or combination of substances selected to act as the stabilizer does not interfere with the interaction between the hydrophobic ionophore and the ion to form the ionophore/ion complex or with the interaction between the ion complex and the hydrophobic reporter substance. Useful stabilizer compounds include water soluble or water-swellable polymers, either synthetic or naturally occurring. In particular, a water-swellable polymer is a slightly crosslinked polymer capable of absorbing several times its weight in water. Suitable synthetic polymers include noncrosslinked and slightly crosslinked polymers, such as noncrosslinked and lightly crosslinked acrylates, poly(vinyl alcohol), copolymers of acrylic acid, carboxymethylcellulose, hydroxybutylcenulose, hydroxyethylcellulose, hydroxypropyleellulose and hydroxymethylcellulose. The hydrophilic polymer compound also can be a naturally occurring polymer, and preferably a naturally occurring polymer that forms a gel when dissolved in water. Such naturally occurring polymers include, but are not limited to, agarose, gelatin, carageenan, alginates, alginic acid, xanthan gums, guar gums, and similar polymers. All of these materials, synthetic and naturally occurring, are water-soluble or water-swellable polymers that, in their dry state, exhibit a marked wettability by aqueous media.

Surprisingly and unexpectedly, an aqueous composition consisting of the hydrophobic ionophore, the hydrophobic reporter substance and the hydrophilic polymer compound can be formed into a film or a layer, or can be incorporated into a suitable hydrophilic carrier matrix, then dried to form a test pad of a test device for use in assaying for the presence or concentration of a predetermined electrolyte in an aqueous test sample. However, the aqueous composition consisting of the hydrophobic ionophore, the hydrophobic reporter substance and the hydrophilic polymer compound also can include optional ingredients such as buffers, surfactants, chelating agents, preservatives, photochemical stabilizers, light scattering centers and background dyes as long as the optional ingredients do not interfere with the production of a detectable change in response to the presence of an electrolyte. Therefore, in accordance with an important feature of the present invention, it is well within the experimental techniques of those skilled in the art of preparing test devices to design a device for the dry phase assay of an electrolyte in an aqueous test sample by varying the relative amounts and relative identity of the hydrophobic ionophore, hydrophobic reporter substance, hydrophilic polymer compound and any optional ingredients to provide a test pad that yields a detectable and differentiable color transition, such that a comparison, either visually or by instrument, to color standards derived from solutions having a standard electrolyte concentration is possible.

For example, the hydrophobic reporter substance can provide a detectable response by loss of a proton upon formation of the ionophore/ion complex. Therefore, a buffering compound can be included to maintain a pH that allows a proton loss from the hydrophobic reporter substance upon an interaction between the ionophore/ion complex and the hydrophobic reporter substance, and that inhibits proton loss from purely pH or other environmental effects. Generally, the desired pH range for proton loss to occur because of an interaction between the ionophore/ion complex and the hydrophobic reporter substance is between about 5 to about 10, but the particular pH choice depends on the hydrophilic indicator reagent composition components, the test sample and the desired sensitivity of the assay. For example, at a higher pH, proton loss occurs more readily, and therefore a higher pH provides an apparent increase in reactivity. At a lower pH, the opposite is true. The desired pH range therefore provides a neutral, essentially completely protonated, hydrophobic reporter substance prior to contact of the hydrophilic indicator reagent composition with the ion of interest. With respect to the preferred colorimetric hydrophobic reporter substances that lose a proton upon interaction with an ionophore/ion complex, the chemical form of the hydrophobic reporter substance, either protonated or unprotonated, usually is evident because the color of the hydrophobic reporter substance changes radically upon conversion from the protonated to the nonprotonated form. The determination of a suitable pH to assay for the predetermined electrolyte of interest is a routine laboratory experiment well within the skill of those trained in the art.

Therefore, to achieve a suitable pH for the assay of the electrolyte of interest a buffering compound can be included, if necessary, in the hydrophilic indicator reagent composition. The buffering compound can be any buffer, or combination of buffers, capable of providing a pH in the range of from about 5 to about 10. The buffering compound is chosen, and acts, to maintain the pH of the aqueous phase, produced by contact of the aqueous test sample with the dry phase test device, within a pH range that facilitates the interaction between the ionophore/ion complex and a hydrophobic reporter substance. The interaction of the ionophore/ion complex with the hydrophobic reporter substance causes the hydrophobic reporter substance to lose a dissociable proton and a detectable response results. The presence of a buffering compound in the aqueous phase allows the proton loss to occur in response to the predetermined electrolyte concentration of the test sample.

Suitable buffers include citrate, lactate, malonate, trichloracetate, sulfosaucylate, tartarate, phosphate, acetate, borate, bis[2-hydroxyethyl-imino]tris[hydroxlmethyl]methane, 1,3-bis(trishydroxymethyl)methylaminopropane, piperazine -N,N'-bis[2-ethanesulfonic acid], N-2hydroethylpiperazine-N'-2-ethanesulfonic acid (HEPES), 4-morpholinoethanesulfonic acid, N,N-bis(2-hydroxyethyl)glycine, piperazine-N,N'-bis(2-hydroxypropane)sulfonic acid (POPSO), 2-([tris-(hydroxymethyl)methyl]amino)ethanesulfonic acid (TES), tris(hydroxymethyl)aminomethane, N-[2-acetamidol-2 -iminodiacetic acid, N-2-hydroxyethyl -piperazine-N'-3-propanesulfonic acid, 3-N-(trishvdroxymethyl) -methylamino-2-hydroxypropanesulfonic acid (TAPSO), tetramethylammonium borate, and tetramethylammonium phosphate.

The preferred pH range for the assay of a particular electrolyte is related to the hydrophobic reporter substance. Therefore, the choice of buffer is determined by the particular hydrophobic reporter substance used in the electrolyte assay, and to some extent by the desired detectable response. For example, when 7-decyl MEDPIN is used as the hydrophobic reporter substance, the preferred pH range is from about 6 to about 8.5. However, when using a hydrophobic reporter substance that has a higher pKa than 7-decyl NIEDPIN, a higher pH range is preferred. Similarly, when a hydrophobic reporter substance having a lower pKa than 7-decyl MEDPIN is used, a lower pH range is preferred. Furthermore, when the detectable response is a color change, the buffer can influence the degree of the detectable response, and a particular buffer can be chosen to provide an optimum color intensity.

For example, using 7-decyl MEDPIN the color change is from orange to blue. At a higher pH, like pH 8.5 to 10, there is a high "blank" reaction and at a lower pH, like pH 5 to 6, there is very little reaction. It should be understood that both pH extremes (i.e., a pH of from 5 to 10) can be used when an instrumental method of detection is used, however the optimum instrumental precision also occurs within the pH range of from about 6 to about 8.5.

The hydrophilic indicator reagent composition also can include a chelating agent to remove interfering substances from the test sample. Although a hydrophobic ionophore usually is chosen because it selectively complexes with the predetermined electrolyte of interest, in some cases other cations interfere with the interaction of the hydrophobic ionophore with the predetermined electrolyte of interest. For example, body fluids normally contain many different cations, such as sodium ion (Na+), potassium ion (K+), calcium ion (Ca++) and magnesium ion (Mg++). Therefore, the presence of different cations could interfere with the assay for a particular ion, such as sodium, because the hydrophobic ionophore does not complex with sodium to the exclusion of complexing with any other cation.

For example, a particular hydrophobic ionophore preferentially can bind to a sodium ion as opposed to a calcium ion in a ratio of approximately 4 to 1. Therefore, in a test sample having a ratio of sodium ion to calcium ion of less than 4 to 1, it may be necessary to prevent the interaction of calcium ions with the hydrophobic ionophore in order to ensure the proper correlation between sodium ion concentration in the test sample and the detectable response. Accordingly, a chelating agent can be included in the hydrophilic indicator reagent composition as an interferant removal compound to eliminate calcium ion interference.

In particular, ethylenediaminetetraacetic acid (EDTA) and ethylene glycol bis(aminoethyl)tetraacetic acid are water-soluble compounds that form complexes with divalent cations, such as calcium ions. If EDTA is included in a hydrophilic indicator reagent composition designed to assay for sodium ion, upon contact with an aqueous test sample containing sodium and calcium ions, the EDTA preferentially complexes with the calcium ions. As a result, the complexed calcium ion is not available to substantially interfere with the formation of the ionophore/sodium ion complex. Therefore, the resulting color change in the hydrophobic reporter substance is due to an interaction essentially only with the ionophore/sodium ion complex to give an accurate and reliable sodium ion assay.

In addition, hydrophobic ionophores can be used to remove interfering cations if they are specific for the interfering cation or if they are chemically-modified to provide some water solubility without decreasing their ability to interact with the interfering cation. For example, an ionophore having aryl moieties can be modified by the addition of water solubilizing functional groups, such as sulfonate (-SO3H) groups, to the aryl moieties to provide some water solubility of the ionophore without decreasing the ability of the ionophore to interact with the interfering ion.

In addition, a hydrophilic surfactant or wetting agent can be included in the hydrophilic indicator reagent composition. In some instances, the addition of a surfactant enhances the operation of the test device. For example, when an aqueous test sample is pipetted onto the test pad of the test device, the test sample can form a liquid bead on the surface of the test device. The addition of a hydrophilic surfactant to the hydrophilic indicator reagent composition can reduce the surface tension of the aqueous test sample thereby allowing the test sample to level out and efficiently and evenly contact the test pad of the test device. Of course, the surfactant must be chosen such that it does not interfere with the formation of the ionophore/ion complex or with the interaction between the ionophore/ion complex and the hydrophobic reporter substance to produce a detectable or measurable response.

The addition of a surfactant to the hydrophihe indicator reagent composition is not always necessary. However, when a surfactant is added, suitable surfactants include, but are not limited to, nonionic surfactants, such as the nonoxyols, the octoxynols and polyoxyethylene ethers of fatty alcohols. Other surfactants, as are well known to those skilled in the art, such as anionic or cationic surfactants, also can be used provided that the surfactant does not interfere with the production of a detectable response to the predetermined electrolyte of interest. Similarly, other optional ingredients like preservatives or background dyes can be added to the hydrophilic indicator reagent composition of the present invention.

As previously described, and as will be evident from the following examples and methods of preparing a test device of the present invention, the hydrophilic indicator reagent composition consists essentially of a hydrophobic ionophore, a hydrophobic reporter substance and a hydrophobic stabilizer compound. The hydrophilic indicator reagent composition, plus any optional ingredients, is dissolved in water, or in water containing a small amount of a water-miscible solvent, such as lower alcohols, like methanol or ethanol; tetrahydrofuran; acetone; and like organic solvents. The concentration of the water-miscable organic solvent in the aqueous solution of the indicator reagent composition is generally less than about 5% by volume, and preferably less than about 4% by volume. Further, the organic solvent is evaporated after incorporating the aqueous solution of the indicator reagent composition into a carrier matrix, or after applying the aqueous solution of the indicator reagent composition, as a film or as a layer, onto a suitable substrate.

In addition, the relative concentration of each of the components of the aqueous solution of the indicator reagent composition is not critical to the invention provided that the concentration of the hydrophobic ionophore, hydrophobic reporter substance and hydrophilic polymer compound each is sufficient to produce a detectable response to the predetermined electrolyte content of the test sample after evaporation of the water and any organic solvent present in the aqueous solution. For qualitative electrolyte assays, neither the concentration of the hydrophobic ionophore nor the concentration of the hydrophobic reporter substance is directly related to the concentration range of the ion to be determined.

Determination of the optimum concentration of the components of the aqueous solution of the hydrophilic indicator reagent composition is within the ability of one skilled in the art of designing dry phase test strips. However, the following concentration ranges are provided to demonstrate the range wherein each component can be included in the aqueous solution of the hydrophilic indicator reagent composition. The concentration of the water-miscible organic solvent usually is kept to a minimum, such as less than about 5% by volume. The concentration of hydrophilic polymer compound can vary widely. Different hydrophilic polymer compounds have drastically different solubility, gelling and film-forming properties, therefore, the amount of hydrophilic polymer compound included in the aqueous solution depends upon the particular physical properties of the hydrophilic polymer compound and the particular physical properties desired in the test pad. The concentration of the optional hydrophilic surfactant is less than the critical micelle concentration for the surfactant because surfactant concentrations above this level tend to produce anomalous results.

However, it has been found that, preferably, the hydrophobic ionophore is present in a molar excess over the hydrophobic reporter substance (i.e., a greater than 1:1 molar ratio of ionophore to reporter substance). It also has been found that the concentration of the hydrophobic ionophore can range from about 2 gm/L (grams per liter) to saturation. The hydrophilic polymer compound usually is present in concentrations ranging from about 10 gm/L to about 100 gm/L. The interferant removing chelating agent, if included at all, is included at levels ranging from 0 gm/L to about 30 gm/L. The concentration of the chelating agent included in the hydrophilic indicator reagent composition usually is related to the concentration of the interfering ion in the test sample of interest. For example, in an assay for lithium ion, the concentration of chelating agent for calcium ion removal is much lower than the concentration of chelating agent required for sodium ion removal. Therefore, the concentration of chelating agent can vary widely, but it is expected that approximately equimolar quantities of the chelating agent to the interfering ion will be used.

The useful and the preferred concentration ranges of the components of an aqueous solution of the hydrophilic indicator reagent composition used in a test pad of electrolyte test devices, using either instrumental or visual detection techniques, are given below. The concentration ranges usually are given in gm/L, or alternatively, in millimolar quantities, to eliminate the differences in molecular weight of various ionophores. Concentrations are given in grams per liter of the aqueous solution of the hydrophilic indicator reagent composition.

|  | Useful | Preferred |
| --- | --- | --- |
| Instrumental Detection |  |  |
| Ionophore | 2-200 gm/L | 5-100 gm/L |
|  | (6-600 mM) | (15-30 mM) |
| Reporter Substance | 1-50 gm/L | 5-30 mg/L |
|  | (2-110 mM) | (10-70 mM) |
| Surfactant | 0-3 gm/L | 0-2 gm/L |
| Buffer | 0-1 M | 0-0.8 M |
| Chelating Agent | 0-30 gm/L | 10-20 gm/L |
| Visual Detection |  |  |
| Ionophore | 2-50 gm/L | 5-15 gm/L |
|  | (3-80 mM) | (7-25 mM) |
| Reporter Substance | .5-5 gm/L | 1.5-4 gm/L |
|  | (1-11 mM) | (3-9 mM) |
| Buffer | 0-1 M | 0-0.7 M |
| Chelating Agent | 0-30 gm/L | 0-20 gm/L |
| Surfactant | 0-3 gm/L | 0-2 gm/L |

To demonstrate the new and unexpected results achieved by the method of the present invention, an aqueous solution of the hydrophilic indicator reagent composition, including the ionophore 2,3-naphtho-15-crown-5, the reporter substance 7-decyl MEDPIN and the stabilizer compound gelatin, was prepared. This aqueous solution can be incorporated into a carrier matrix that, after drying, is used as a test pad in a dry phase test strip assay for determining the presence or concentration of an electrolyte in an aqueous test sample. Alternatively, a layer of the aqueous solution can be applied directly to a suitable substrate, then, after drying, the resulting film of the hydrophilic indicator reagent composition is used as a test pad in a dry phase test strip assay for determining the presence or concentration of a particular electrolyte in an aqueous test sample.

In addition to preparing a test device several methods of preparing an aqueous solution of the hydrophilic indicator reagent composition were discovered. It was found that the most straightforward methods, such as those suggested by Feinstein et al., did not produce a homogeneous aqueous solution of the hydrophilic indicator reagent composition. Neither dissolving the components of the hydrophilic indicator reagent composition directly in a buffer solution having a suitable pH nor dissolving the hydrophilic indicator reagent composition in a water-miscible organic solvent and then adjusting the pH with a buffer having the desired pH, thereby also diluting the organic solvent concentration to produce an aqueous solution containing less than about 5% by volume organic solvent, produced a homogeneous, aqueous solution capable either of incorporation into a suitable carrier matrix or of being applied as a film or layer to form a test pad for measuring the concentration of a predetermined ion at clinically significant levels. Distinctly different methods of producing a homogeneous aqueous solution of the hydrophilic indicator reagent composition were found and are described below.

In order to prepare the desired homogeneous, aqueous solution two steps essential. First, it is necessary to prepare a high pH aqueous solution of the hydrophobic ionophore and hydrophobic reporter substance. Then a second aqueous solution of the high pH aqueous solution and the hydrophilic polymer must be formed at the working pH. There are at least two ways of making the first, high pH solution. (a) The hydrophobic ionophore and the hydrophobic reporter substance are dissolved directly in a high pH aqueous solution with mixing. (b) The hydrophobic ionophore and the hydrophobic reporter substance are dissolved in a water miscible organic solvent. This solution is then added with mixing to a large volume of a high pH aqueous solution. There are also at least two ways of making the second, working pH solution. (i) The high pH solution is mixed with a solution containing low pH buffer and hydrophilic polymer to give a mixture with the working pH. (ii) The high pH solution is mixed with an aqueous solution of the hydrophilic polymer. The resulting solution is then mixed with a low pH buffer solution to give a mixture with the working pH.

A high pH solution is one where the reporter molecule is anionic due to a loss of a proton, typically one or more pH unites above the effective dissociation pK for this proton. For 7-decyl-MEDPIN this pH would be about 10 and the solution would be blue. A high pH solution of tetrabromophenolphthalein decyl ester would be about 7 and the color of the solution would also be blue. It is believed that in the presence of the high pH aqueous solution the hydrophobic reporter substance acts to solubilize the hydrophobic ionophore thereby unexpectedly permitting the hydrophobic materials to form an aqueous solution.

A working pH solution is one where the reporter molecule is largely neutral and the pH is one or two pH units below the effective pK of the dissociable proton. For 7-decyl-MEDPIN this pH would be about 6.5 and the solution would be red. A working pH solution for tetrabromophenolphthalein decyl ester would be about 4 and the color would be yellow.

Mixing can be accomplished by any suitable means such as the use of a motor/stir bar combination, an impeller-type stirrer or vortexing. The resulting hydrophilic reagent composition is optically clear. However, if some particulate matter remains this can be removed by mild centrifugation.

For example, in one suitable method, the hydrophobic ionophore and the hydrophobic reporter substance are dissolved in a water-miscible organic solvent as the first step in preparing a homogeneous aqueous solution. After the ionophore and reporter substance are dissolved in a water-miscible organic solvent, the resulting organic solvent-based solution then is added, with stirring, to an aqueous, alkaline solution having a pH sufficiently high to cause dissociation of the dissociable proton from the reporter substance. For a colorimetric reporter substance, this proton dissociation usually is easily observed because the color of the dissociated form of the reporter substance is different from the color of the neutral form of the reporter substance. The pH of the high pH aqueous alkaline solution then is adjusted by adding an auquot of the solution containing the dissociated reporter substance to an aqueous solution having a pH in the range wherein the reporter substance is in the neutral form. Consequently, the reporter substance now is present in the aqueous solution in the neutral form. The dissociation of the reporter substance can reoccur upon formation of a ionophore-/ion complex resulting from contact between the test sample and the hydrophilic indicator reagent composition. It should be noted that the water-miscible organic solvent can be chosen from any of the solvents that dissolve the ionophore and the reporter substance in the desired concentrations. For example, tetrahydrofuran (THF), acetone, methanol and ethanol have been used successfully. However, THF is the preferred organic solvent.

Example 1 specifically demonstrates the formation of an aqueous solution of a hydrophilic indicator reagent composition that can be incorporated into a suitable carrier matrix, or applied as a film to a suitable substrate, then dried and used as a test pad to detect and measure ion concentrations in solution.

EXAMPLE 1

Aqueous Solution of a Hydrophilic Indicator Reagent Composition for Detection and Measuring Potassium Ion Concentrations A homogeneous aqueous solution suitable for forming a test pad of a test device used to assay for potassium ions was prepared according to the procedure described in the general method. In this particular aqueous solution, 2,3-naphtho-15-crown-5 was used as the ionophore; 7-decyl-MEDPIN was used as the reporter substance; and gelatin was used as the stabilizer compound. In particular, a homogeneous organic solvent-J based solution first was prepared by dissolving a sufficient amount of the 2,3-naphtho-15-crown-5 and of the 7-decyl-MEDPIN in tetrahydrofuran (THF) such that each component was present at a concentration of 200 mM. Then, to 5 ml of a 50 mM aqueous solution of lithium hydroxide was added 500 uL (microliters) of the homogeneous organic solvent-based solution of the ionophore and the reporter substance, with vortexing. The resulting aqueous solution was blue in color, and the ionophore and the reporter substance present at concentrations 1/10 of their original concentration. The resulting blue, aqueous solution then was mixed with 1. 67 ml of a 20% by weight aqueous gelatin solution to produce another clear blue solution than can be incorporated into a suitable carrier matrix or applied onto a suitable substrate as a film.

As stated above, the aqueous solution of the hydrophilic indicator reagent composition can be used to form the test pad of the test device. The test pad of the present invention can be produced by one of two methods. In the first method, the aqueous solution of the hydrophilic indicator reagent composition is applied as a film, such as with a Meyer rod, directly to a suitable substrate. The substrate should be sufficiently hydrophilic, or, if hydrophobic, possess a sufficiently rough or sufficiently treated surface, such that the hydrophilic indicator reagent composition can sufficiently adhere to the substrate surface. The wet film then is dried to form a test pad of the hydrophilic indicator reagent composition comprising the ionophore, the reporter substance and the stabilizer compound. Alternatively, the aqueous solution of the hydrophilic indicator reagent composition first is incorporated into a suitable bibulous or nonbibulous carrier matrix, like filter paper, glass fibers, or a layer or film of a polymeric material. Then, the carrier matrix incorporating the hydrophilic indicator reagent composition is dried to yield a test pad for assaying an aqueous test sample for a predetermined electrolyte concentration.

More particularly, in one embodiment of the present invention, the aqueous solution of the hydrophilic indicator reagent composition of Example 1 was coated, such as stripe-coated, directly onto a plastic substrate, such as polystyrene, with a #75 Meyer rod to provide a film having a thickness of $6.75 \times 10^{-3}$ inches. After removing the aqueous solvent, and any organic solvent, by drying in an air oven at about 50° C. for about 20 to 30 minutes, the dried film of the hydrophilic indicator reagent composition served as the test pad of a test device for a predetermined electrolyte, i.e., potassium, in an aqueous test sample. Alternatively, the aqueous composition can be applied to a film support, like a polyester film, that can accept gelatin. Such a polyester film is available commercially from 3M Co., St. Paul, Minn. under the brandname to 40 GA8 25.

In either case, the test device is a test strip, designed either as a single pad test strip (to assay only for a single analyte) or as a multiple pad test strip (to assay for several analytes simultaneously), including a support strip, or handle, normally constructed from a hydrophobic plastic, and a test pad comprising the hydrophihe indicator reagent composition. The handle usually is formed from hydrophobic materials such as cellulose acetate, polyethylene terephthalate. polycarbonate or polystyrene. The aqueous solution of the hydrophilic indicator reagent composition can be coated onto a suitable substrate, then dried to form a test pad on the suitable substrate. This test pad and substrate can be secured to the handle by a double-sided adhesive. Preferably, the aqueous solution of the hydrophilic indicator reagent composition initially is applied to a handle of suitable construction as a stripe-coated wet film. Drying the aqueous solution of the hydrophilic indicator reagent composition forms the test pad of the present invention. In this embodiment, the test pad is formed directly on the handle of the test device.

The handle of the test device can be opaque, or it can transmit light or other energy. When the detectable response is fluorescence, or if an optional layer is placed over the upper surface of the test pad of the test device to allow any excess test sample to be wiped off, the test device can be read through a transparent support material. A transparent support material is especially useful in the assay of whole blood. The optional layer over the upper surface of the test pad can be used to filter, or otherwise separate, the cellular components of the whole blood sample from the serum or plasma. The serum or plasma then can migrate to the test pad to interact with the hydrophilic indicator reagent composition, and bottom surface of the transparent handle can be examined for a detectable response. This particular test device allows a small whole blood sample to be assayed without the need to separate the cellular components from the serum or plasma prior to the assay.

Therefore, preferred handles include transparent materials capable of transmitting electromagnetic radiation of a wavelength in the range of about 200 nanometers (nm) to about 900 nm. The support need not transmit over the entire 200-900nm region, although for fluorometric detection it is desirable that the support be transparent over a band wider than, or at least equal to, the absorption and emission spectra of the fluorescent materials used for detection. It also may be desirable to have a support that transmits one or more narrow wavelength bands and is opaque to adjacent wavelength bands. This could be accomplished, for example, by impregnating or coating the support with one or more colorants having suitable absorption characteristics.

In another embodiment of the present invention, the aqueous solution of the hydrophilic indicator reagent composition of Example 1 first is incorporated into a suitable hydrophilic carrier matrix. The carrier matrix incorporating the hydrophilic indicator reagent composition then is dried to form a test pad of the present invention. The test pad then is secured to a plastic handle of the same construction as described above to produce a test device of the present invention. Sindlarly, an optional coating can be applied above the test pad to separate the cellular material from a whole blood sample.

In this embodiment of the present invention, the hydrophilic carrier matrix is an absorbent material that allows the hydrophilic indicator reagent composition to move, in response to capillary forces, through the matrix to homogeneously incorporate the hydrophilic indicator reagent composition into the matrix. Subsequent contact with a test sample produces a detectable or measurable color transition in response to the predetermined electrolyte concentration of the test sample. The carrier matrix can be any substance capable of incorporating the chemical reagents required to perform the assay of interest, as long as the carrier matrix is substantially inert with respect to the chemical reagents, and is porous or absorbent relative to the liquid test sample.

The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, sintered ceramic frits, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulosic beads, and especially fiber-containing papers such as filter paper or chromatographic paper; synthetic or modified naturally-occurring polymers, such as cellulose acetate, polyacrylamide, polyacrylates, polyurethanes, crosslinked dextran, agarose and other such crosslinked and noncrosslinked water-insoluble hydrophilic polymers. Hydrophobic and nonabsorptive substances are not suitable for use as the carrier matrix of the present invention. The carrier matrix can be of different chemical compositions or a mixture of chemical compositions. The matrix also can vary in regards to smoothness and roughness combined with hardness and softness. However, in every instance, the carrier matrix should include a hydrophilic or absorptive material.

In accordance with this embodiment of the present invention, to perform a dry phase, test strip assay for an electrolyte, an aqueous solution of the hydrophilic indicator reagent composition of Example 1 first is prepared. A suitable carrier matrix, such as filter paper, then is saturated with the aqueous solution of the hydrophilic indicator reagent composition either by spreading, by immersing or by spraying the aqueous solution onto sheets or precut strips of the filter paper. After removing the aqueous solvent by oven drying in an air oven at about 500° C. for about 20 to 30 minutes, the filter paper incorporating the hydrophilic indicator reagent composition is cut to an appropriate size, such as a pad having dimensions from about 0.25 cm by about 0.5 cm to about 0.5 cm by about 1.0 cm. The filter paper incorporating the hydrophilic indicator reagent composition then is secured to an opaque or transparent hydrophobic plastic handle with double-sided adhesive tape, available from 3M Company, St. Paul, Minn.

The devices of the present invention can be adapted to carry out a wide variety of chemical analyses, not only in the field of clinical chemistry, but in chemical research and chemical process control laboratories. The devices are especially well-suited for use in clinical testing of body fluids, such as blood, plasma, serum, cerebrospinal fluid, and urine, because a large number of repetitive assays are frequently conducted and assay results often are needed within a very short time. In regard to the analysis of blood, the present invention can be adapted for use in performing a quantitative analysis for blood electrolytes of clinical interest, such as potassium, sodium, magnesium or calcium. The present invention provides a particularly useful test for the determination of serum potassium wherein the assay for low concentrations of potassium requires measurements of high sensitivity and high precision. Similarly, the present invention provides a very useful test for the determination of serum lithium in individuals undergoing a lithium treatment for depression. Such a lithium test is extremely important because the clinically useful dose of lithium is close to a toxic dose of lithium, therefore lithium levels in the blood must be carefully monitored.

The test device is used by contacting the test device with a test sample for a sufficient period of time. In the case of whole blood or urine testing, merely dipping the test device into the sample is sufficient. Although it is usually unnecessary to remove excess sample, in some cases, such as with whole blood samples, any excess test sample, or the cellular components of the whole blood sample separated from the plasma or serum by an optional coating layer over the test pad, is removed by wiping or blotting.

If the predetermined ion of interest is present in the test sample, the resulting ionophore/ion complex interacts with the reporter substance, and the response, like a color transition, is detected and measured. When the reporter substance is a proton dissociable compound, wherein a dissociated compound having a different color from the undissociated compound is produced, an observable color change forms in the test device that can be visually or instrumentally monitored. If a transparent handle is used, the observable color change can be monitored from either side of the device. In the case of a whole blood sample, the observable color change is monitored from the bottom surface of the transparent handle. If the reporter substance is a fluorophore, such as fluorescein or a fluorescein derivative, a fluorescence spectrophotometer can be utilized to measure the detectable response formed in the test device (i.e., the appearance of or the change in fluorescence). Other techniques useful in observing a detectable response include reflectance spectrophotometry, absorption spectrophotometry and light transmission measurements.

Various calibration techniques are applicable as a control for the assay of the predetermined assay of interest. For example, a sample of a standard solution of a particular electrolyte can be applied to a separate test device as a comparison or to permit the use of differential measurements in the analysis. Test devices can be designed that are suitable for quantitative visual determinations when an appropriate color chart is supplied.

In accordance with either embodiment of the present invention, the test strip was dipped into an aqueous test sample for a sufficient time to insure sufficient contact of the test pad with the test sample. After waiting a predetermined time, such as from about 30 seconds to 360 seconds, the test strip is examined, either visually or by instrument, for a detectable response. The color transition, if any, of the test pad reveals the presence or concentration of the predetermined electrolyte of interest in the aqueous test sample.

Analogous to designing the aqueous solution of the hydrophilic indicator reagent composition as described above, it is well within the experimental techniques of those skied in the art of preparing test devices to determine the proper balance between size of the test pad, the strength of aqueous solution of the hydrophilic indicator reagent composition, the amount of test sample, and the method of introducing the test sample to the test strip, such as by pipetting rather than dipping, in order to design a quantitative assay for a predetermined electrolyte utilizing the method and test device of the present invention.

In many cases, such as in qualitative assays, simple visual observation of the test strip provides the desired information. If more accurate information is required, a spectrophotometer or colorimeter can be used to more precisely determine the intensity and degree of the color transition. In addition, the dry phase test strip assay can be made quantitative by employing spectrophotometric or colorimetric techniques, as opposed to visual techniques, in order to more reliably and more accurately measure the intensity and degree of the color transition, and therefore more accurately measure the concentration of a predetermined electrolyte in the aqueous test sample, especially at the lower, clinically-significant electrolyte concentrations, such as below 10 mM, and especially below about 2 mm.

Figure 1:
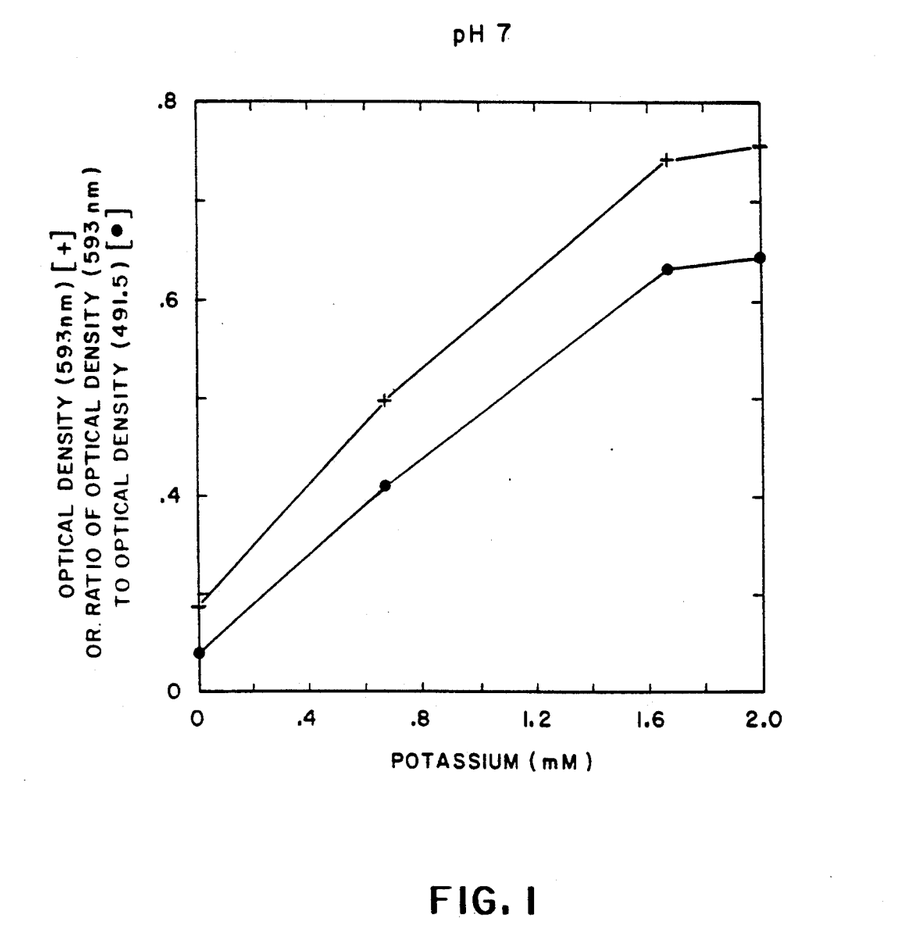
The drawing is a graph of potassium ion concentration in mMol/L vs. optical density measured at 593nm (manometers), and a graph of potassium ion concentration vs. the ratio of the optical density measured at 593nm to the optical density measured at 491.5nm, the isospestic point.

To demonstrate the utility of the present invention in the assay of a predetermined electrolyte, the reddish-orange, buffered aqueous solution of the hydrophilic indicator reagent composition of Example 1 was applied directly, as a stripe-coated film, to a hydrophobic plastic handle, constructed of GEL BOND, available from Marine Colloids, with a #75 Meyer rod. The wet film was allowed to dry in an air oven, as described above, to form a test pad directly on the plastic handle. The resulting test strip was used to assay standardized aqueous solutions containing known amounts of potassium ion. As demonstrated in FIG. 1, standardized aqueous solutions containing potassium ions ranging in concentration of from 0 MM to 2.0 mM were assayed for potassium ion concentration with test devices of the present invention. After allowing the test device to contact the standardized solution for about 30 sec., the color transition response was detected and measured by normal spectroscopic transmission techniques. FIG. 1 shows that the plot of absorbance (optica-I density or OD) at 593nm (the blue form) vs. potassium ion concentration is essentially linear, especially over the concentration range of 0 MM to about 1.75 mM. Therefore, the unknown potassium ion concentration of a test sample can be determined from this graph of absorption (OD) vs. potassium ion concentration for known standard solutions.

The second plot of FIG. 1 is a plot of potassium ion concentration of standardized solutions vs. the ratio of the absorbance of the test strip at 593nm to the absorbance of the test strip at 491.5 nm, the isospestic point. The isospestic point is defined as the wavelength wherein the extinction coefficient for both the protonated form and the deprotonated form of the indicator are identical. This plot corrects variations in test pad film thickness. This plot also is essentially linear, especially over the potassium concentration range of 0 mM to about 1.75 mM, therefore allowing a more accurate determination of potassium ion concentration in a test sample.

In regard to the assay of a whole blood sample for a predetermined electrolyte, five cations having particular clinical significance can be assayed by the method and device of the present invention. However, it should be understood that other cations present in a whole blood sample, and in general other cations present in other test samples, also can be assayed by the method and device of the present invention by the selection of a suitable ionophore and a suitable reporter substance. This selection is easily performed by a person of ordinary skill in the art of designed diagnostic test strips.

The five cations, potassium, sodium, lithium, magnesium and calcium, are present in the blood in different concentrations. For example, sodium generally is present in the blood in amounts ranging from 120 mM to 170 mM, and normally in the range of from about 135 mM to about 155 mM. Likewise, potassium generally is present in amounts ranging from about 2 MM to about 10 mM, and normally from about 3.5 mM to about 5.5. The normal ranges for magnesium and calcium in the blood are about 0. 5 mM to about 1. 5 mM, and about 2 mM to about 3 MM respectively. Lithium normally is not found in the blood, however an individual undergoing lithium therapy for depression should maintain a serum lithium level of from about 0.6 mM to about 1. 2 mm.

The device and method of the present invention can assay for each of these ions in the clinically- significant concentration ranges without diluting the blood sample. An undiluted blood sample especially can be used to assay for magnesium and lithium because these ions are present in such low amounts. Furthermore, the linearity of the graphs presented in FIG. 1 over the range of from 0 mM to about 1. 75 mM shows that accurate and sensitive assays for these ions can be achieved. Assays for calcium, potassium and sodium also can be performed on undiluted blood samples, but because of the greater concentration of these ions in the blood and because of the linearity of the test method demonstrated in the range of from 0 mM to 1. 75 mM of ion, the assays for these ions also can be performed on diluted whole blood, diluted serum or diluted plasma samples.

For example, in the assay for calcium, the neat, undiluted whole blood sample can be assayed, or the sample can be diluted with up to two parts of water per part of whole blood sample. This dilution rate provides a diluted blood sample having a calcium level of about 1 mM calcium. Similarly, in an assay of whole blood for potassium ions, the whole blood sample can be diluted with 5 parts of water per part of blood sample to provide a sample including about 1 MM of potassium ions. Finally, in the assay for sodium, diluting the whole blood sample with up to 50 times with water provides a test sample including about 1 mM in sodium ions. The above dilution ratios for the different cations provide a test sample having a sufficient amount of ion for detection and an amount of ion in the concentration region of FIG. 1 showing the most accurate response of the hydrophilic indicator reagent composition to the predetermined ion of interest, i.e. from 0 mM to about 1.75 mM of ion in the test sample.

The method and test device of the present invention therefore affords an economical, accurate and reliable assay for the concentration of a predetermined electrolyte in an aqueous test sample. The assay can be performed at home or in the laboratory. In addition, the method of the present invention allows detection, differentiation and measurement of low electrolyte concentrations in the test sample, such as from 0 mM to about 10 mM, therefore making the assay more useful clinically. Moreover, the test device of the present invention, by avoiding the use of an organic hydrophobic phase, eliminates a costly and time-consuming step in the manufacture of the dry phase test strip.

More importantly, the method and test device of the present invention allows the detection and measurement of the concentration of a predetermined electrolyte by simple and accurate absorption/transmission measurements on a single layer test device. As a result, the costly and time-consuming manipulative steps that are required to manufacture multilayer test devices can be avoided. The single layer test device thereby allows, a simple dip-and-read assay procedure, as opposed to the prior art electrolyte assays using a hydrophobic phase that utilized less accurate reflectance techniques to assay for electrolyte concentration in aqueous test samples. However, the method and test device of the present invention also can be used to assay for whole blood when a layer of suitable material is positioned over the test strip to filter or otherwise separate the cellular components of the whole blood sample from the plasma or serum.

The method and test device of the present invention provide rapid assay results with a detectable response exhibited within a few minutes. Cumbersome and expensive testing equipment is not required. In addition, the detectable response is of sufficient magnitude to enable direct visual detection. Moreover, it has been found that the color or other detectable response produced in the test device is usually stable, in some instances for a period of days, such that a number of used test devices can be set aside for reading at some future time.

Therefore, in accordance with an important feature of the present invention, more accurate and reliable assays for the concentration of a predetermined electrolyte in whole blood, plasma, serum and other aqueous test samples can be performed by utilizing a hydrophilic indicator reagent composition. The hydrophilic indicator reagent composition provides sufficient color resolution to perform an accurate assay and improves assay sensitivity by allowing the electrolyte concentration to be determined by absorbance/transmission detection techniques as opposed to reflectance techniques. The use of absorbance/transmission techniques also allows the use of a single layer test device that is more economical to manufacture than the multilayer test strips required for reflectance measurements.

Obviously, many modifications and variations of the invention as hereinbefore set forth can be made without departing from the spirit and scope thereof and therefore only such limitations should be imposed as are indicated by the appended claims.

What is claimed is:

1. A hydrophilic indicator reagent composition for determining the presence or concentration of an electrolyte, which composition consists essentially of:
   (a) a hydrophobic ion-specific ionophore capable of forming a complex with a specific ion to be determined,
   (b) a hydrophobic reporter substance capable of interacting with said complex of said ionophore and a specific ion to be determined to produce a detectable response, and
   (c) a hydrophilic polymer compound.

2. A method of determining the presence or concentration of a predetermined ion in a test sample comprising:
   (a) contacting the test sample with an analyte detection device, wherein said analyte detection device includes a hydrophilic test pad impregnated with a homogeneous hydrophilic indicator reagent composition consisting essentially of:
      (i) a hydrophobic ion-specific ionophore capable of forming a complex with the predetermined ion;
      (ii) a hydrophobic reporter substance capable of interacting with said complex formed by the ionophore and the predetermined ion to provide a detectable response; and
      (iii) a hydrophilic polymer compound;
   (b) examining the analyte detection device for a detectable response; and
   (c) correlating the detectable response to the concentration of the predetermined ion in the test sample.

3. The method of claim 2 wherein the hydrophobic reporter substance is selected from the group consisting of a phenol, an indophenol compound, a triphenylmethane, a fluorescein, a fluorescein ester, a 7-hydroxy coumarin, a resorufin, a pyren-3-ol, a flavone and combinations thereof.

4. The method of claim 3 wherein the hydrophobic reporter substance is p-nitrophenol, tetrabromophenolphthalein decyl ester, methyl eosin, phenolphthalein, bromocresol purple, cresophthalein, chlorophenol red, tetrabromophenol blue, thymophthalein, eosin-5-maleamic acid, 7-(n-decyl)-2-methyl-4-(3',5'-dichlorophen-4'-one)indophenol, 2-methyl-4-(3',5'-dichlorophen-4'-one)indonaphth-l-ol, or combinations thereof.

5. The method of claim 2 wherein the hydrophilic polymer is selected from the group consisting of agarose, gelatin, carageenan, an alginate, alginic acid, a xanthan gum, a guar gum, an acrylate, a poly(vinyl alcohol), a copolymer of acrylic acid, carboxymethylcellulose, hydroxybutycellulose, hydroxyethylcellulose, hydroxypropylcellulose, hydroxymethylcellulose and combinations thereof.

6. The method of claim 2 wherein the hydrophobic ion-specific ionophore is selected from the group consisting of a coronand, a podand, valinomycin, a macrotetralide actin, monenesin, and combinations thereof.

7. The method of claim 2 wherein the concentration of the predetermined ion in the test sample is determined and said concentration is in the range of from 0 millimolar to about 200 millimolar.

8. The method of claim 2 wherein the predetermined ion is potassium ion and the hydrophobic ion-specific ionophore is selected from the group consisting of 15-crown-5; 2,3-naphtho-1,4,7,10,13-pentaoxacyclopentadeca-2-ene; valinomycin; 4,7,13,16,21,24-hexaoxa-1,10-diaza-bicyclo[8,8,8]hexacosane; 18-crow-n-6; dibenzo-18-crown-6; dicyclohexano-18-crown-6 and combinations thereof.

9. The method of claim 2 wherein the predetermined ion is sodium ion and the hydrophobic ion-specific ionophore is selected from the group consisting of 15-crown-5; 1,1,1-tris[1',(2'-oxa-4'-oxo-5'-aza-5'-methyl)-dodecanyl]propane; N,N'-dibenzyl-N,N'-diphenyl-1,2-phenylenedioxydiacetamide; 6,7,9,10,18,19-hexahydro-17-n-butyl dibenzol[b,k][1,4,7,10,131-pentaoxacyclohexadecane-18-yl-oxyacetic acid; 4,7,13,16,21-pentaoxa-1,10-diaza-bicyclo[8,8,5]tricosane; bis[12-crown-4-methyllmethyldodecylmalonate; monenesin and combinations thereof.

10. The method of claim 2 wherein the predetermined ion is lithium ion and the hydrophobic ion-specific ionophore is selected from the group consisting of N,N'-diheptyl-N,N',5,5-tetramethyl-3,7-dioxanonane diamide; cis-N,N,N',N'-tetraisobutyl-1,2-cyclohexane dicarboxamide; N,N'-diheptyl-5,5-dimethyl-N,N'-di(3-oxapentyl)-3,7-dioxanane diamide; 12-crown-4; 4,7,13,18-tetraoxa-1,10-diaza-bicyclo[8,5,5]eicosane and combinations thereof.

11. The method of claim 2 wherein the predetermined ion is magnesium ion and the hydrophobic ion-specific ionophore is N,N'-diheptyl-N,N'-dimethyl-1,4-butanediamide.

12. The method of claim 2 wherein the predetermined ion is calcium ion and the hydrophobic ion-specific ionophore is diethyl-N,N'-[(4R,5R-4,5-dimethyl-1,8-dioxo-3,6-dioxaoctamethylene]-bis(12-methylaminododecanoate).

13. The method of claim 2 wherein the test pad further comprises a buffer capable of providing a pH in the range of from about 4 to about 9.

14. The method of claim 2 wherein the test pad further comprises a chelating agent, a hydrophilic surfactant or a combination thereof.

15. The method of claim 2 wherein the hydrophobic ion-specific ionophore and the hydrophobic reporter substance are present in a molar ratio of hydrophobic ion-specific ionophore to hydrophobic reporter substance of greater than one.

16. The method of claim 2 wherein the hydrophilic test pad further comprises a hydrophilic carrier matrix.

17. The method of claim 16 wherein the hydrophilic carrier matrix is selected from the group consisting of filter paper, chromatographic paper, cellulosic beads, a hydrophilic crosslinked polymer and combinations thereof.

18. The method of claim 2 wherein the predetermined ion is potassium ion, the hydrophobic ion-specific ionophore is a coronand, the hydrophobic reporter substance is 7-(n-decyl)-2-methyl-4-(3',5'-dichlorophen-4'-one)indophenol, and the hydrophilic polymer compound is gelatin.

19. The method of claim 18 wherein the coronand is 2,3-naphtho-1,4,7,10,13-pentaoxacyclopentadeca-2-ene;

20. An analyte detection device to determine the presence or concentration of a predetermined ion in a liquid test sample comprising:
   (a) a support strip; and
   (b) a hydrophilic test pad operatively connected to the support strip said hydrophilic test pad comprising:
   (c) a hydrophilic indicator reagent composition consisting essentially of:
      (i) a hydrophobic ion-specific ionophore capable of forming a complex with the predetermined ion;
      (ii) a hydrophobic reporter substance capable of interacting with a complex of the hydrophobic ionophore and the predetermined ion to provide detectable response; and (iii) a hydrophilic polymer compound.

21. The analyte detection device of claim 20 wherein the hydrophilic test pad further comprises a buffer capable of providing a pH in the range of from about 4 to about 9, a chelating agent, a hydrophilic surfactant or a combination thereof.

22. A test pad for determining the presence of or the concentration of specific ion in a test sample, said test pad comprising a layer of hydrophilic indicator reagent composition, said hydrophilic indicator reagent composition consisting essentially of:

(i) a hydrophobic ion-specific ionophore capable of forming a complex with a specific ion to be determined;

(ii) a hydrophobic reporter substance capable of interacting with the complex of the hydrophobic ionophore and the specific ion to produce a detectable response; and (iii) a hydrophilic polymer compound.

23. The test pad of claim 22 wherein the reporter substance includes a dissociable proton.

24. The test pad of claim 22 wherein the hydrophilic polymer is selected from the group consisting of agarose, gelatin, carageenan, an alginate, alginic acid, a xanthan gum, a guar gum, an acrylate, a poly(vinyl alcohol), a copolymer of acrylic acid, carboxymethylcellulose, hydroxybutycellulose, hydroxyethylcellulose, hydroxypropylcellulose, hydroxymethylcellulose and combinations thereof.

25. A method of manufacturing a hydrophilic indicator reagent composition for determining the presence or concentration of a predetermined ion in a liquid test sample, said method comprising the steps of:

(a) preparing a high pH aqueous solution of a hydrophobic ion-specific ionophore capable of forming a complex with the predetermined ion and a hydrophobic reporter substance capable of interacting with the complex of the hydrophobic ionophore and a predetermined ion to provide a detectable response and then forming a second aqueous solution from the first aqueous solution and a hydrophilic polymer.

26. The composition of claim 1 wherein the hydrophobic reporter substance is selected from the group consisting of a phenol, an indophenol compound, a triphenylmethane, a fluorescein, a fluorescein ester, a 7-hydroxy coumarin, a resorufin, a pyren-3-ol, a flavone and combinations thereof.

27. The composition of claim 1 wherein the hydrophilic polymer is selected from the group consisting of agarose, gelatin, carageenan, an alginate, alginic acid, a xanthan gum, a guar gum, an acrylate, a poly(vinyl alcohol), a copolymer of acrylic acid, carboxymethylcellulose, hydroxybutycellulose, hydroxyethylcellulose, hydroxypropylcellulose, hydroxymethylcellulose and combinations thereof.

28. The composition of claim 1 wherein the hydrophobic ion-specific ionophore is selected from the group consisting of a coronand, a podand, valinomycin, a macrotetralide actin, monenesin, and combinations thereof.

29. The composition of claim 1 wherein the concentration of the electrolyte is in the range of from 0 millimolar to about 200 millimolar.

30. The composition of claim 1 wherein the electrolyte is potassium ion and the hydrophobic ion-specific ionophore is selected from the group consisting of 15-crown-5; 2,3-naphtho-1,4,7,10,13-pentaoxacyclopentadeca-2-ene; valinomycin; 4,7,13,16,21,24-hexaoxa-1,10-diazabicyclo[8,8,8]hexacosane; 18-crown-6; dibenzo-18-crown-6; dicyclohexano-18-crown-6 and combinations thereof.

31. The composition of claim 1 wherein the electrolyte is sodium ion and the hydrophobic ion-specific ionophore is selected from the group consisting of 15-crown-5; 1,1,1-tris[1',(2'-oxa-4'oxo-5'-aza-5'-methyl)-dodecanyl]propane; N,N'-dibenzyl-N,N'-diphenyl-1,2-phenylenedioxydiacetamide; 6,7,9,10,18,19-hexahydro-17-n-butyl dibenzol[b,k][1,4,7,10,13]-pentaoxacyclohexadecane -18-yl-oxyacetic acid; 4,7,13,16,21-pentaoxa-1,10-diazabicyclo[8,8,5]tricosane; bis[12-crown-4-methyl]methyldodecylmalonate; monenesin and combinations thereof.

32. The composition of claim 1 wherein the electrolyte is lithium ion and the hydrophobic ion-specific ionophore is selected from the group consisting of N,N'-diheptyl-N,N',5,5-tetramethyl-3,7-dioxanonane diamide; cis-N,N,N',N'-tetraisobutyl-1,2-cyclohexane dicarboxamide; N,N'-diheptyl-5,5-dimethyl-N,N'-di(3-oxapentyl) -3,7-dioxane diamide; 12-crown-4; 4,7,13,18-tetraoxa -1,10-diazabicyclo[8,5,5]eicosane and combinations thereof.

33. The composition of claim 1 wherein the electrolyte is magnesium ion and the hydrophobic ion-specific ionophore is N,N'-diheptyl-N,N'-dimethyl -1,4-butanediamide.

34. The composition of claim 1 wherein the electrolyte is calcium ion and the hydrophobic ion-specific ionophore is diethyl-N,N'-bis(12-methylaminododecanoate).

35. The composition of claim 1 wherein the hydrophobic ion-specific ionophore and the hydrophobic reporter substance are present in a molar ratio of hydrophobic ion-specific ionophore to hydrophobic reporter substance of greater than one.

36. The composition of claim 1 wherein the electrolyte is potassium ion, the hydrophobic ion-specific ionophore is a coronand, and the hydrophobic reporter substance is 7-(n-decyl)-2-methyl-4-(3',5'-dichlorophen-4'-one)indophenol.

37. The composition of claim 36 wherein the coronand is 2,3-naphtho-1,4,7,10,13-pentaoxacyclopentadeca-2-ene.

* * * * *

UNITED STATES PATENT AND TRADEMARK OFFICE
CERTIFICATE OF CORRECTION

PATENT NO.   : 5,300,439
DATED        : April 5, 1994
INVENTOR(S)  : Steven C. Charlton It is certified that error appears in the above-identified patent and that said Letters Patent is hereby corrected as shown below:

Col. 27, line 66, "18-crow-n-6;" should be --18-crown-6--;

Col. 28, line 7, "dibenzol [b,k] [1,4,7, 10, 131-pentaoxacy-" should be --dibenzol [b,k] [1,4,7,10,13]-pentaoxacy--

Col. 28, line 10, "4-methyllmethyldodecylmalonate" should be --4-methyl] methyldodecylmalonate--;

Col. 30, line 34, "-3,7-dioxane diamide" should be --3,7-dioxanonane diamide--;

Col. 30, lines 43-44, "diethyl-N-N'-bis (12 methylaminododecanoate)" should be --diethyl-N,N' - [(4R,5R-4, 5-dimethyl-1,8-dioxo-3,6-dioxaoctamethylene]-bis(12-methylaminododecanoate)--.

Signed and Sealed this

Third Day of June, 1997

Attest:

BRUCE LEHMAN

Attesting Officer

Commissioner of Patents and Trademarks